(12) United States Patent
Calton et al.

(10) Patent No.: US 8,729,463 B2
(45) Date of Patent: May 20, 2014

(54) MEASUREMENT OF 25-HYDROXYVITAMIN D3 AND C3-EPI-25-HYDROXYVITAMIN D3

(75) Inventors: Lisa J. Calton, Stockport (GB); Billy J. Molloy, Bramhall (GB)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 13/637,392

(22) PCT Filed: Mar. 28, 2011

(86) PCT No.: PCT/GB2011/050624
§ 371 (c)(1),
(2), (4) Date: Oct. 17, 2012

(87) PCT Pub. No.: WO2011/121342
PCT Pub. Date: Oct. 6, 2011

(65) Prior Publication Data
US 2013/0126721 A1 May 23, 2013

Related U.S. Application Data

(60) Provisional application No. 61/346,496, filed on May 20, 2010.

(30) Foreign Application Priority Data

Mar. 29, 2010 (GB) .................. 1005315.5

(51) Int. Cl.
*H01J 49/00* (2006.01)
*G01N 33/82* (2006.01)
*H01J 49/04* (2006.01)
*G01N 30/72* (2006.01)
*G01N 30/02* (2006.01)
*G01N 30/34* (2006.01)
*G01N 30/36* (2006.01)

(52) U.S. Cl.
CPC ......... *H01J 49/0431* (2013.01); *H01J 49/0031* (2013.01); *H01J 49/0027* (2013.01); *G01N 30/7233* (2013.01); *G01N 30/02* (2013.01); *G01N 30/34* (2013.01); *G01N 30/36* (2013.01); *G01N 33/82* (2013.01)
USPC ....................................................... 250/288

(58) Field of Classification Search
CPC .............. H01J 49/0027; H01J 49/0031; H01J 49/0431; G01N 30/7233; G01N 30/72; G01N 30/02; G01N 33/82; G01N 30/36; G01N 30/34; B01J 20/287; B01J 20/288; B01D 15/325
USPC .................................. 250/281, 282, 283, 288
See application file for complete search history.

(56) References Cited

U.S. PATENT DOCUMENTS

| | | | |
|---|---|---|---|
| 4,551,624 A | 11/1985 | Spangler et al. | |
| 5,014,009 A | 5/1991 | Arimoto et al. | |

(Continued)

OTHER PUBLICATIONS

Molly et al. "A New Semi-Automated Solid-Phase Extraction Method for the High-Through-Put Analysis of 25-Hydroxyvitamin D in Serum", Waters, Application note pp. 1-4, copy write 2009.*

(Continued)

*Primary Examiner* — Michael Logie
(74) *Attorney, Agent, or Firm* — Waters Technologies Corporation

(57) ABSTRACT

The invention describes a method of quantification of an analyte selected from the group consisting of 25-hydroxyvitamin D3 and C3-epi-25-hydroxyvitamin D3 in a specimen containing the analyte; comprising the steps of subjecting the specimen to UPLC reverse-phase separation; and; detecting the protonated precursor pseudo-molecular ion of the analyte using a mass spectrometry technique to determine the amount of the analyte.

19 Claims, 5 Drawing Sheets

(56) References Cited

U.S. PATENT DOCUMENTS

| | | | |
|---|---|---|---|
| 5,801,380 | A | 9/1998 | Sinha |
| 6,163,031 | A | 12/2000 | Abdel-Rahman |
| 6,734,964 | B1 | 5/2004 | Duan et al. |
| 7,417,226 | B2 | 8/2008 | Bajic et al. |
| 7,972,867 | B2 * | 7/2011 | Clarke et al. .................. 436/173 |
| 2006/0228809 | A1 * | 10/2006 | Clarke et al. .................. 436/173 |
| 2007/0151910 | A1 * | 7/2007 | Boschetti et al. ........... 210/198.2 |
| 2010/0043101 | A1 * | 2/2010 | Yamaguchi et al. ........... 800/279 |
| 2011/0201039 | A1 * | 8/2011 | Barr et al. ........................ 435/23 |
| 2011/0315633 | A1 * | 12/2011 | Cormier et al. ............... 210/656 |

OTHER PUBLICATIONS

Carcinogenesis, "Liquid chromatography-electrospray ionization-mass spectrometry: the future of DNA adduct detection" Carcinogensis (Feb. 2006).*

Schug "Pseudo-Molecular Ion Formation by Aromatic Acid in Negative ionization mode electrospray ionization mass spectrometry" Oct. 2002.*

Agilent Zorbax SB-CN data sheet (2003).*

Chasteen, Coupling Gas Chromatography Mass Spectrometry, Sam Houston State University, 2009, (retrieved Jan. 25, 2013) Retrieved from internet URL: http://www.shsu.edu/-chm_tgc/primers/gcms.html—entire document.

Molloy, et al; [Application Note] A New Semi-Automated Solid-Phase Extraction Method for the High-Through-Put Analysis of 25-Hydroxyvitamin D in Serum; Waters Corporation, 4 pages, Jul. 2009.

Calton, et al; [Application Note]; The Analysis of 25-Hydroxyvitamin D in Serum Using UPLC/MS/MS; Waters Corporation, 4 pages, Oct. 2008.

Singh, et al; C-3 Epimers Can Account for a Significant Proportion of Total Circulating 25-Hydroxyvitamin D in Infants, Complicating Accurate Measurement and Interpretation of Vitamin D Status, Journal of Clinical Endocrinolgy Metabolism, 91(8) pp. 3055-3061, Aug. 2006.

Aronov, et al; Metabolic profiling of major vitamin D metabolites using Diels-Alder derivatization and ultra-performance liquid chromatography-tandem mass spectrometry; Anal bioannal Chem (2008) 391:1917-1930, 2008.

Ferse, et al; Chromatographie; Methodenumstellung von HPLC auf UPLC; 3 Pages, 2005.

Knox, et al; A simple automated solid-phase extraction procedure for measurement of 25-hydroxyvitamin D3 and D2 by liquid chromatography-tandem mass spectrometry; Annals of Clinical Biochemistry, vol. 4G, 6 pages, May 2009.

Wallace, et al; Measurement of 25-hydroxyvitamin D in the clinical laboratory: Current procedures, performance characteristics and limitations; Steriods 75 (2010) 477-488.

Tsugawa et al; Determination of 25-Hydroxyvitamin D in Human Plasma Using High-Performance Liquid Chromatography-Tandem Mass Spectrometry; Anal. Chem 2005, 77, 3001-3007.

Vogeser, et al; Candidate Reference Method for the Quantification of Circulating 25-Hydroxyvitamin D3 by Liquid Chromatography-Tandem Mass Spectrometry; Clinical Chemistry 50, No. 8, 3 pages, 2004.

Eyles, et al; A sensitive LC/MS/MS assay of 25OH vitamin D3 and 25OH vitamin D2 in dried blood spots,Clinica Chimica Acta, 403 (2009) 145-151.

Holmoy, et al; 25-Hydroxyvitamin D in cerebrospinal fluid during relapse and remission of multiple sclerosis; Research Paper; Multiple Sclerosis, 7 pages, 2009.

PCT International Search Report for Application No. PCT/US2012/068663, filed Dec. 10, 2012, 4 pages, dated Feb. 8, 2013.

PCT International Written Opinion Report for Application No. PCT/US2012/068663, 7 pages, dated Feb. 8, 2013.

* cited by examiner

MEASUREMENT OF 25-HYDROXYVITAMIN D3 AND C3-EPI-25-HYDROXYVITAMIN D3

This invention relates to the separation and quantification of the C3-epimer of 25-hydroxyvitamin D3 (25OHD3) in serum or other specimens.

Vitamin D is a generic designation for a group of fat-soluble structurally similar sterols. Vitamin D compounds are derived from dietary ergocalciferol (from plants, vitamin D2) or cholecalciferol (from animals, vitamin D3), or by conversion of 7-dihydrocholesterol to vitamin D3 in the skin upon UV-exposure. Vitamin D2 and D3 are subsequently 25-hydroxylated in the liver to form 25-hydroxyvitamin D2 (25OHD2) and 25-hydroxyvitamin D3 (25OHD3). 25OHD2 and 25OHD3 represent the main body reservoir and transport form of vitamin D. They are stored in adipose tissue or are tightly bound by a transport protein while in circulation, and are subsequently hydroxylated to the corresponding 1,25 dihydroxy forms in the kidney. 1,25-dihydroxyvitamin D2 (DHVD2) and 1,25-dihydroxyvitamin D3 (DHVD3) are potent calciotropic hormones involved in the regulation of both calcium and phosphate metabolism, and are inhibitors of parathyroid hormone (PTH).

Vitamin D laboratory testing has increased significantly during the last decade because of an increasing awareness that vitamin D deficiency is very common and can increase fracture and, possibly, cancer risk. Measurement of total 25-hydroxyvitamin D (25OHD; the sum of 25OHD2 and 25OHD3) is the preferred test for assessing vitamin D status, because it has a long serum half-life and its concentration is considered to be in equilibrium with vitamin D body stores.

Unfortunately, there have been substantial discrepancies between test results obtained with different 25OHD assays. Most 25OHD assays are competitive immunoassays or competitive assays based on vitamin D binding proteins. For such assays, 25OHD is a difficult analyte because of its hydrophobicity and relatively low serum concentrations. This often necessitates sample extraction and concentration before analysis, potentially increasing assay variability. Furthermore, equal detection of 25OHD2 and 25OHD3 represents a challenge, in particular for assays based on vitamin D binding protein, because binding proteins from many species show higher affinity for 25OHD3 than for 25OHD2. As a consequence of all these factors, only 50-60% of the approximately 100 laboratories that participate in the international quality assessment scheme for vitamin D metabolites (DEQAS), meet the performance criteria consistently, and the results obtained for the same sample can differ up to 2- to 4-fold, sometimes even for the same assay, when performed in different laboratories.

It is known from WO 2010/019566 that methods can be used to measure the levels of DHVD2, DHVD3, or both (total DHVD) in a sample. For example, DHVD2 and DHVD3 can be selectively and sensitively detected and quantitated using methods employing affinity purification, analyte derivatization, and mass spectrometric (MS) techniques. WO 2010/019566 discloses that the combination of the affinity purification and analyte derivatization steps eliminates sample interferences, provides increased sensitivities, and provides more accurate results than methods that employ only analyte derivatization and concludes that the disclosed methods can facilitate reliable quantification of both DHVD2 and DHVD3 to 5 pg/ml or lower. The materials and methods are said to be useful to aid in the diagnosis of vitamin D deficiencies or hypervitaminosis D, to monitor vitamin D replacement therapies, and to aid in the diagnosis of various disorders, e.g., hypercalcemia, chronic renal failure, hypoparathyroidism, sarcoidosis, granulomatous diseases, malignancies, primary hyperparathyroidism, and physiologic hyperarathyroidism.

The C3-epimer of 25-hydroxyvitamin D3 (C3-epi-25OHD3) is an optical isomer of 25OHD3. This optical isomer is of clinical interest because it can cause interference to an assay quantifying 25OHD3.

According to the present invention there is provided a method of quantification of an analyte selected from the group consisting of 25-hydroxyvitamin D3 and C3-epi-25-hydroxyvitamin D3 in a specimen containing the analyte; comprising the steps of subjecting the specimen to UPLC reverse-phase separation; and;

detecting the protonated precursor pseudo-molecular ion of the analyte using a mass spectrometry technique to determine the amount of the analyte.

Preferred embodiments of the present invention provide a method of using UPLC reverse-phase separation of 25OHD3 from C3-epi-25OHD and the MRM detection of the protonated precursor pseudo-molecular ion to the fragmented product ion. Electrospray ionisation is preferably used.

The present invention further relates to UPLC reverse-phase chromatographic separation of 25-hydroxyvitamin D3 (25OHD3) from C3-epi-25OHD to facilitate determination of a C3-epimer concentration in an analyte. The analyte may be taken from the adult population. When employing a reverse phase LC/MS/MS method the C3-epimer co-elutes with 25OHD3 because they are optical isomers. A chiral chromatography method has been used to separate these compounds. However, the chromatographic separation was poor. The Standard Reference Material published by NIST describes a candidate reference procedure for the measurement of 25OHD in serum using extended reverse phase chromatography, where the baseline resolution of the C3-epimer from 25OHD3 was demonstrated using extended chromatography. Use of chromatography over an extended period is not conveniently applicable to routine clinical assay.

The present invention seeks to provide a shorter time for the analysis by chromatographic separation in order to make this assay applicable to routine clinical analysis.

The present invention preferably uses solid phase extraction (SPE). This facilitates automation of the process. Liquid-liquid extraction may also be used.

The NIST procedure has a retention time which is too long for clinical use. The present invention may provide a 12 minute run time, suitable for clinical assay.

The UPLC column may have a particle size of 1.8 µm or below.

The epimer is separated by UPLC. The stereoisomers are separated by ion mobility MS. Reverse phase chromatography at UPLC pressures may be used.

An internal standard can be added to the sample prior to determination of the analyte.

The use of a labelled isotope of the epimer as an internal standard may be avoided. Deuterated 25OHD2 may be used as an internal standard. When using the chromatography conditions of this invention.

The sample may be a biological sample such as a tissue, for example adipose tissue, liver, kidney, heart, muscle, bone or skin tissue, or a biological fluid, for example, blood, serum, plasma, urine, lachrymal fluid or saliva. Dried blood spot analyses may be employed. The biological sample may be obtained from a mammal, for example a human, dog, cat, primate, rodent, pig, sheep, cow or horse.

The sample may be treated to remove components that interfere with the mass spectrometry technique. Solid samples can be ground, purified and extracted to release the analytes from interfering components. The sample may be centrifuge filtered or subjected to chromatographic techniques, for example using solid phase extraction columns to remove interfering components. Reagents may be added to precipitate, bind or dissociate impurities or interfering components. For example, whole blood samples can be treated using convention clotting techniques. Samples may be deproteinised. For example, a plasma sample can have serum proteins precipitated using conventional reagents such as acetonitrile or alkali followed by centrifugation of the sample. Methanol or other organic solvent may be used.

After sample preparation, the sample can be subjected to a mass spectrometry (MS) technique. A mass spectrometry technique can use atmospheric pressure chemical ionization (APCI) in the positive ion mode or electrospray ionization (ESI) to generate precursor positive ions. Analytes of interest can exist as charged species, such as protonated molecular ions $[M°+H^+]$ or $[M+H^+]$ in the mobile phase. During the ionization phase, the molecular ions are desorbed into the gas phase at atmospheric pressure and then focused into the mass spectrometer for analysis and detection.

MS analysis can be conducted with a single mass analyzer (MS) or a "tandem in space" analyzer such as a triple quadrupole tandem mass spectrometer (MS/MS). Using MS/MS, the first mass filter (Quadrople 1, Q1) can select, or can be tuned to select, independently, one or more of the molecular ions of the analyte, and the internal standard (if any). The second mass filter (Q3) is tuned to select specific product or fragment ions related to the analyte of interest. Between these two mass filtration steps, the precursor molecular ions can undergo collision-induced dissociation (CID) at Q2 to produce product or fragment ions. The previously described mass spectrometry technique can also be referred to as multiple reaction monitoring, or MRM. In multiple reaction monitoring, both quadrupoles Q1 and Q3 can be fixed (or tuned) each at a single mass, whereas Q2 can serve as a collision cell.

The precursor $[M+H^+]$ or $[M°+H^+]$ ions of the analytes or internal standards typically produce product ions that are shown in Table 1. Accordingly, precursor-product ion-pair transition can be 401.35/159.1 for 25OHD3, 401.35/365.3 for 25OHD3 (Qual), 404.35/162.1 for $d_3$-25OHD3, 413.35/355.3 for 25OHD2, 413.35/83.1 for 25OHD2 (Qual) and 413.36/358.3 for $d_3$-25OHD2.

The methods described herein can be used in various diagnostic applications to monitor vitamin D related pathologies, vitamin D and calcium homeostasis and vitamin D replacement therapies.

The invention is further described by means of example, but not in any limitative sense, with reference to the accompanying drawings, of which:

Figure 1:
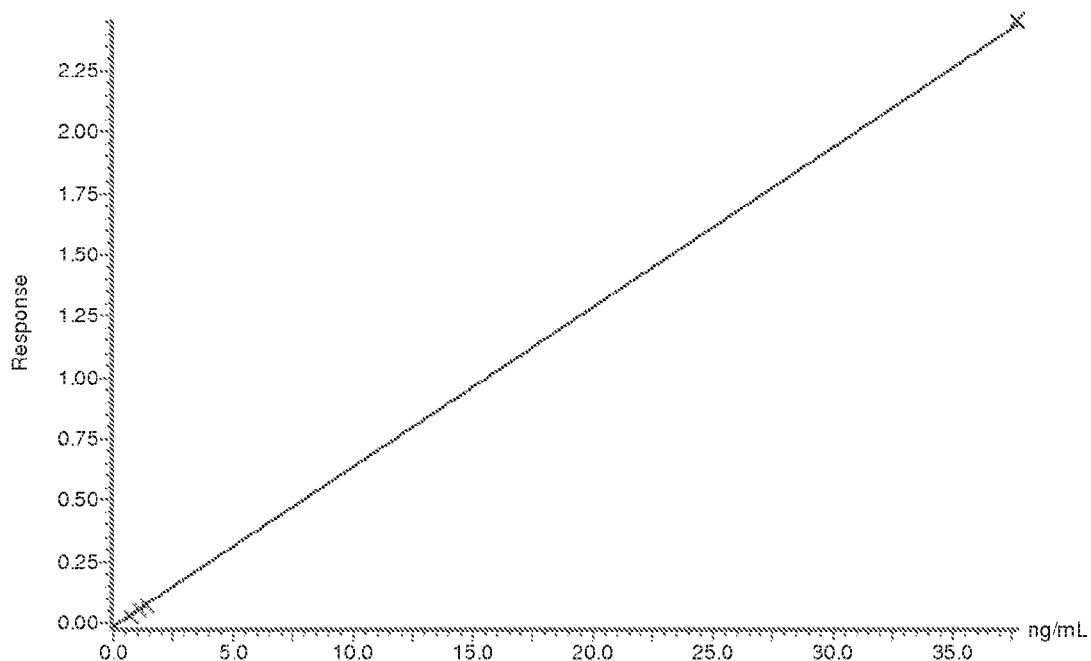
FIG. 1 is a calibration curve of C3-epi-25OHD3.

The following methods were employed:
UPLC
Mobile phase A: Water with 2 mM ammonium acetate+0.1% formic acid
Mobile Phase B: MeOH with 2 mM ammonium acetate+0.1% formic acid
Weak wash solvent: 65% Mobile Phase B, 35% Mobile Phase A, 600 μL
Strong wash solvent: 100% Mobile phase B, 200 μL
Seal Wash: 20% MeOH aq
Column: Agilent Zorbax SB-CN 2.1×50 mm 1.8 μm
Column temp: 35° C.
Injection Vol: 20 μL (PLNO, 50 μl loop and 250 μl sample syringe fitted) 3 μL overfill, load ahead
Flow Rate: 0.25 mL/min
Gradient:

| Time/min | A % | B % | curve |
|---|---|---|---|
| 0 | 40 | 60 | 1 |
| 12.5 | 2 | 98 | 10 |
| 16.5 | 40 | 60 | 11 |

A solvent gradient curve may be used. Preferably a Waters (RTM) gradient curve was employed. A convex curve, most preferably a Waters 10 curve may be used.

Run time: 20 mins

Shorter run times for the chromatographic separation are desirable for routine clinical analyses. Shorter run times enable quicker sample turn-around and increased throughput. This was achieved by using the Waters UPLC chromatography system which used a 1.8 μm particle size column packing material. A reduced flow rate was employed as this required less solvent to be used.

TQD Parameters

The instrument was tuned for unit resolution for MS1 (0.7 Da FWHM) and the resolution for MS2 (0.8-0.9 Da FWHM).

| MS Conditions | |
|---|---|
| Polarity | ES+ |
| Capillary (kV) | 1.2 |
| Cone (V) | 20.00 |
| Extractor (V) | 3.00 |
| RF (V) | 0.1 |
| Source Temperature (° C.) | 120 |
| Desolvation Temperature (° C.) | 400 |
| Cone Gas Flow (L/hr) | 20 |
| Desolvation Gas Flow (L/hr) | 1000 |
| Collision Gas Flow (ml/min) | 0.15 |
| LM 1 Resolution | 14.9 |
| HM 1 Resolution | 14.9 |
| Ion Energy 1 | 0.1 |
| MSMS Mode Entrance | 0.00 |
| MSMS Mode Collision Energy | see MRM Table 1 |
| MSMS Mode Exit | 0.50 |
| LM 2 Resolution | 13.5 |
| HM 2 Resolution | 13.5 |
| Ion Energy 2 | 1.0 |

TABLE 1

MRM transitions for the analysis of 25OHD2 and 25OHD3 and the deuterated internal standards, transitions in italics are optional qualifier ions.

| Compound | MRM | Dwell (secs) | Cone Voltage (V) | Collision Energy (eV) |
|---|---|---|---|---|
| 25OHD3 | 401.35 > 159.1 | 0.08 | 20 | 28 |
| *25OHD3 (Qual)* | *401.35 > 365.3* | *0.08* | *20* | *10* |
| $d_3$-25OHD3 | 404.35 > 162.1 | 0.08 | 20 | 28 |
| 25OHD2 | 413.35 > 355.3 | 0.08 | 20 | 8 |
| *25OHD2 (Qual)* | *413.35 > 83.1* | *0.08* | *20* | *22* |
| $d_3$-25OHD2 | 416.35 > 358.3 | 0.08 | 20 | 8 |

Interscan Scan Delay (secs):0.02
Interscan Channel Delay (secs):0.01

It is noted that: C3-epi-25OHD3 is isobaric and therefore is detected in the same transitions as 25OHD3.

The use of specific fragment ions to perform quantitative analysis was preferred to increase the specificity of the analysis. Additional qualitative ion transitions were monitored to provide a quantifier/qualifier ratio for added confidence of compound identity.

Sample Preparation
Standards

Tri-deuterated 25OHD2 and 25 OHD3 were purchased from IsoSciences. Each 1 mg portion was dissolved in 1 mL of ethanol to produce a 1 mg/mL standard. The 1 mg/mL standards were stored at −20° C. until required.

The working internal standard solution was prepared by adding 50 µL, of each 1 mg/mL IS to 900 µL of MeOH/IPA (80/20 v/v) to give a final concentration of 50 µg/mL (solution A). 50 µL, of solution A was diluted in 9.95 mL of MeOH/IPA to produce a 250 ng/mL working IS solution.

Calibrators

NIST SRM 972 levels 1-4 were used as calibrators and were extracted with 51 anonymized adult serum samples.

The tri-deuterated 25OHD2 was used as an internal standard as it eluted closer to the retention time for the C3-epimer and therefore compensated for any matrix effects upon the ionisation of the molecule. Preferably a stable isotopically labelled C3-epimer is used as the calibrator. This provided improved compensation for any matrix effects that may have been present when the C3-epimer eluted from the chromatography column into the mass spectrometer.

Serum calibrators and samples were extracted using either the LLE or SPE protocols outlined below.

Liquid-Liquid Extraction

Add 150 µL of serum to 2 ml Anachem microtubes
Add 100 µL IS: 250 ng/ml of $d_3$-25OHD3 and $d_3$-25OHD2 (80% MeOH/20% IPA)
Vortex 10 secs
Add 150 µL 0.2 M $ZnSO_4$ aq
Vortex 10 secs
Add 300 µL MeOH
Vortex 10 secs,
Add 750 µL hexane
Vortex 30 secs,
Centrifuge 13,000 rpm for 5 mins
Remove 650 µL of the top organic layer (hexane) into 2 mL Waters maximum recovery vial
Dry down under nitrogen at 50° C.
Reconstitute in 75 µL MeOH/water (65/35 v/v), vortex for 10 secs
Inject 20 µL Oasis HLB µElution SPE Extraction Add 150 µL of serum (sample, calibrator, QC) to a 2 mL deep well 96 well-plate or eppendorf
Add 20 µL IS: 250 ng/ml of $d_3$-25OHD3 and $d_3$-25OHD2 (80%MeOH/20%IPA)
Vortex 1 min
Add 150 µL 0.2 M $ZnSO_4$ aq
Vortex 1 min
Add 600 µL MeOH
Vortex 5 mins,
Centrifuge plate 2,000 rpm for 5 mins
SPE Oasis HLB µElution
Conditioning: 200 uL methanol
Equilibration: 200 uL 60% methanol aq
Load Sample: 600 uL of supernatant from above sample preparation.
Wash 1: 200 uL 5% methanol aq
Wash 2: 200 uL 60% methanol aq
Elution 1: 80 uL 95/5 methanol/IPA
Elution 2: 50 uL water.
(Elute into Waters 1 mL 96 well-plate)
Mix plate well (vortex for 3 mins)
Inject 20 µL The solid phase extraction method was preferred as this allowed the extraction procedure to be automated using an off line liquid handling system.

Results

The following data was generated using the SPE protocol automated on a Tecan liquid-handling system.

A typical calibration line generated using NIST SRM 972 levels 1-4 is shown in FIG. 1.

Figure 2:
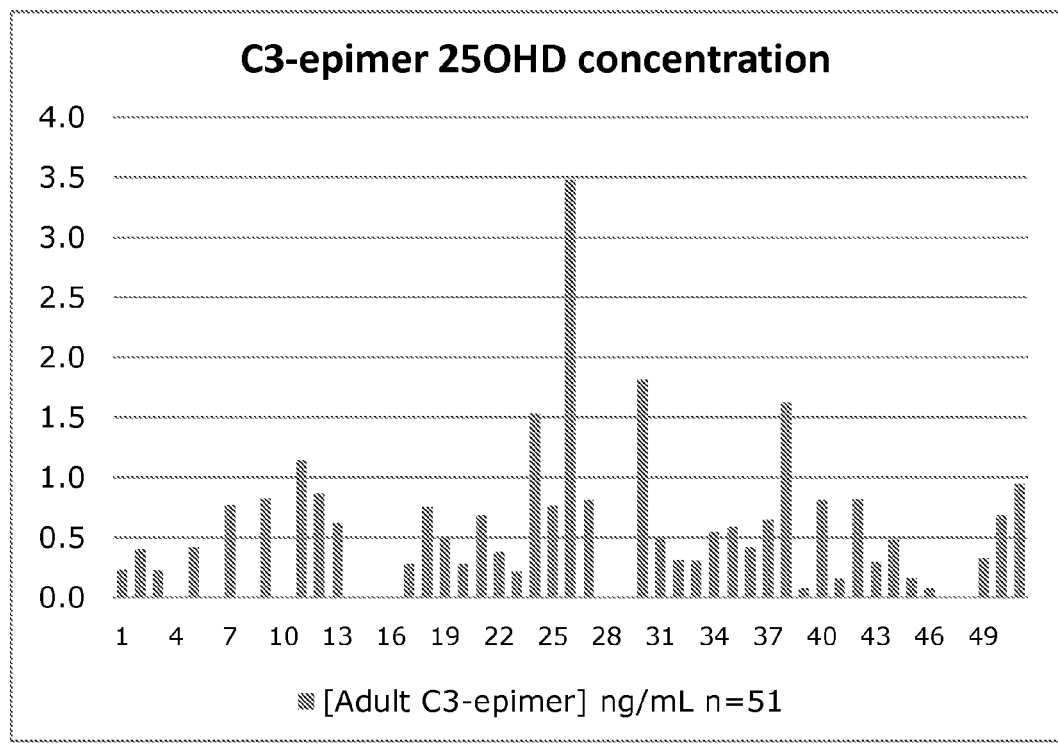
FIG. 2 is a graph showing the C3-epi-25OHD3 concentration in adult serum samples.

The concentrations of C3-epi-25OHD3 quantified in 51 patient samples are shown in FIG. 2.

The majority of samples gave a result of 1 ng/ml indicating that measurable levels were present in most adult human serum samples.

Figure 3:
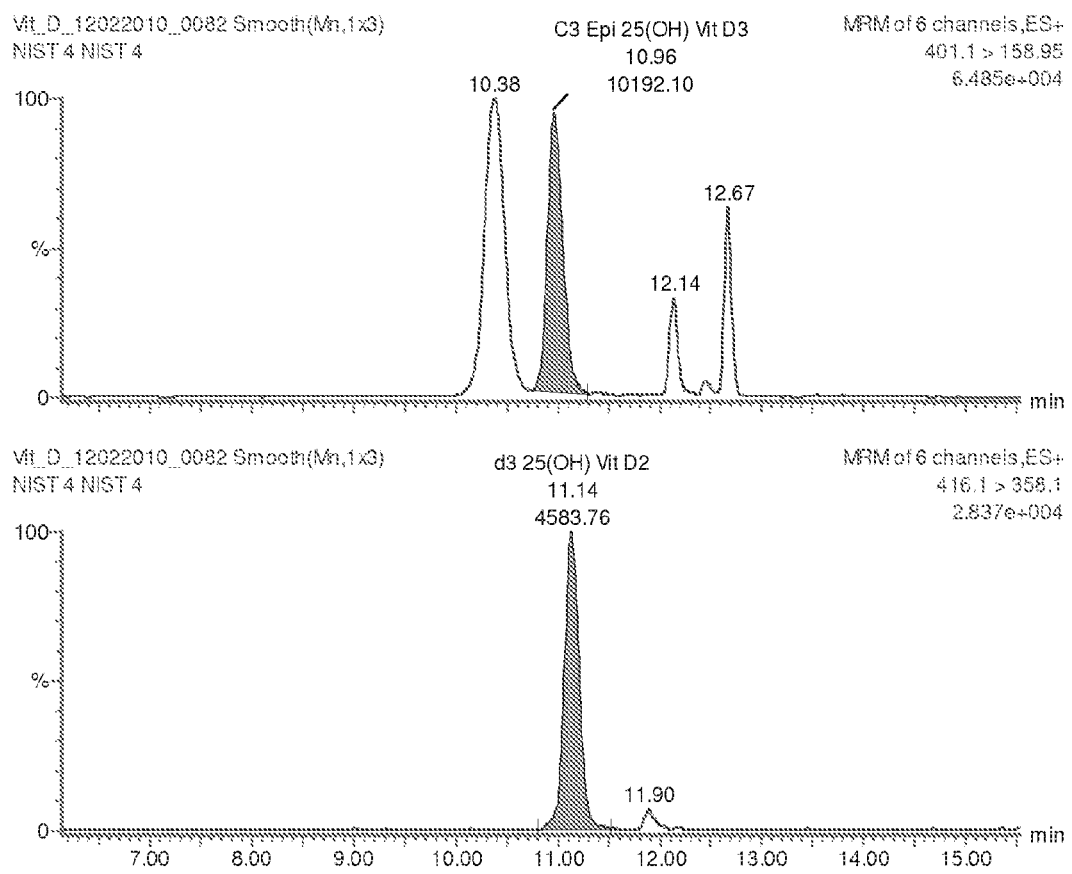
FIG. 3 is a chromatogram showing separation of 25OHD3 from the optical isomer C3-epi-25OHD3.

FIG. 3 shows a chromatogram of NIST SRM 972 levels containing 37.7 ng/mL of C3-epi-25OHD3.

Figure 4:
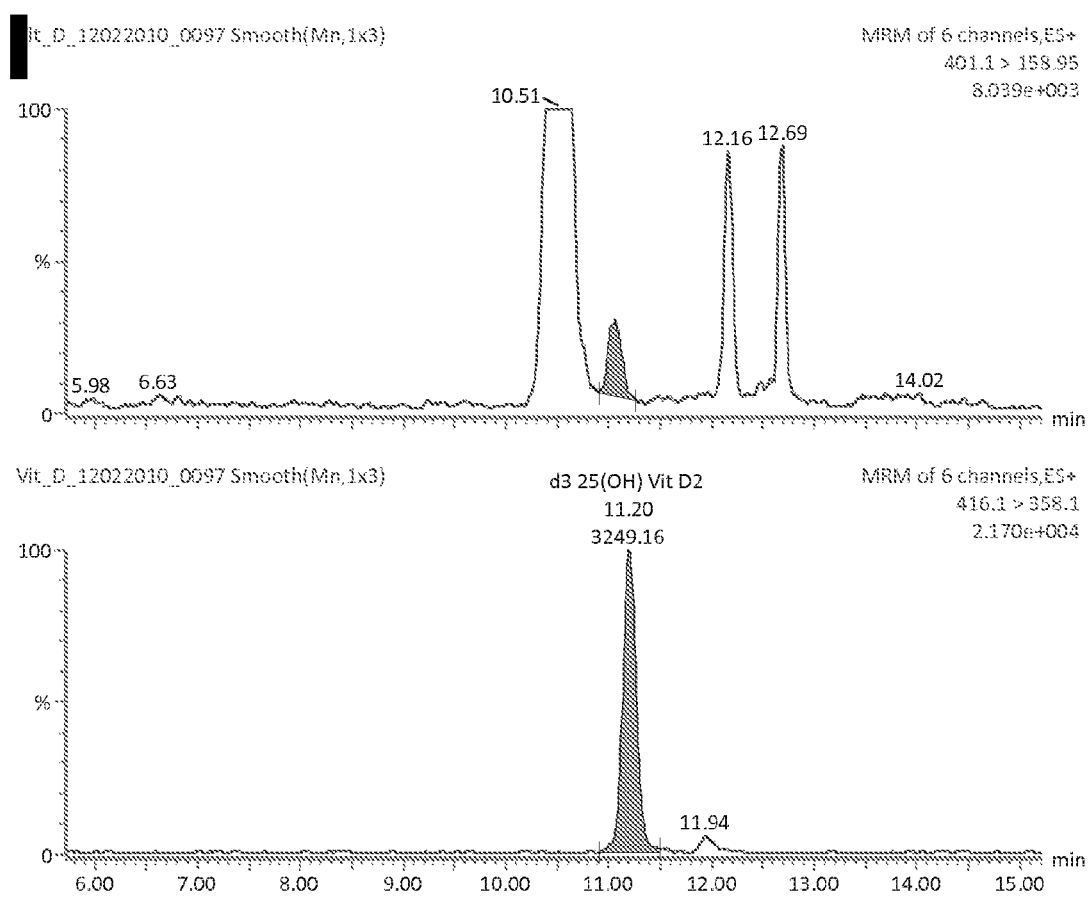
FIG. 4 is a chromatogram of an adult serum sample containing C3-epi-25OHD3.
Figure 5:
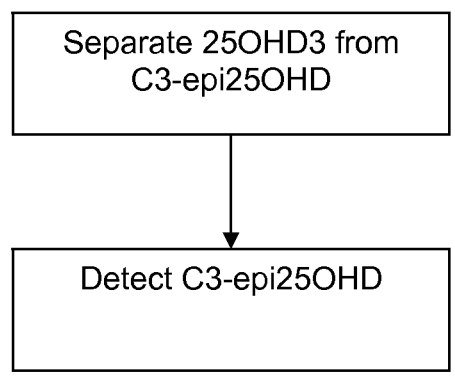
FIG. 5 illustrates an exemplary method according to sn embodiment of the invention.

FIG. 4 shows a chromatogram of an adult serum containing 1.81 ng/mL of C3-epi-25OHD3 (patient sample 30).

The invention claimed is:

1. A method of quantifying C3-epi-25-hydroxyvitamin D3 in a sample containing 25-hydroxyvitamin D3 and C3-epi-25-hydroxyvitamin D3, the method comprising:
   separating the 25-hydroxyvitamin D3 from the C3-epi-25-hydroxyvitamin D3, the separation comprising subjecting the sample to reverse-phase liquid chromatographic separation employing a convex solvent gradient curve and using a non-chiral reverse-phase column, wherein the column includes a stationary phase having a polar functional group, and
   detecting the C3-epi-25-hydroxyvitamin D3 using a mass spectrometry technique to determine at least one of a concentration and an amount of the C3-epi-25-hydroxyvitamin D3in the sample.

2. The method of claim 1, wherein the mass spectrometry technique comprises MRM detection of a protonated precursor pseudo-molecular ion of the C3-epi-25-hydroxyvitamin D3.

3. The method of claim 1, wherein the separation further comprises solid phase extraction.

4. The method of claim 1, wherein the separation step further comprises ion mobility spectrometry.

5. The method of claim 1, wherein the sample is a biological sample.

6. The method of claim 1, wherein deuterated 25OHD2 is added to the sample as an internal standard.

7. The method of claim 1, wherein the liquid chromatographic mobile phases comprise water and methanol.

8. The method of claim 1, wherein the stationary phase is a cyano stationary phase.

9. The method of claim 1, wherein the separation provides baseline resolution of the 25-hydroxyvitamin D3 and the C3-epi-25-hydroxyvitamin D3 in a run time less than about 20 minutes.

10. A method of quantifying C3-epi-25-hydroxyvitamin D3 in a sample containing 25-hydroxyvitamin D3 and C3-epi-25-hydroxyvitamin D3, the method comprising:
    separating the 25-hydroxyvitamin D3 from the C3-epi-25-hydroxyvitamin D3, the separation comprising subjecting the sample to reverse-phase liquid chromatographic separation using a non-chiral reverse-phase column, the column including a stationary phase having a polar functional group, the separation providing baseline resolution of the 25-hydroxyvitamin D3 and the C3-epi-25-hydroxyvitamin D3 in a run time less than about 20 minutes, and detecting the C3-epi-25-hydroxyvitamin D3 using a mass spectrometry technique to determine at least one of a concentration and an amount of the C3-epi-25-hydroxyvitamin D3 in the sample.

11. The method of claim 10, wherein the mass spectrometry technique comprises MRM detection of a protonated precursor pseudo-molecular ion of the C3-epi-25-hydroxyvitamin D3.

12. The method of claim 10, wherein the separation further comprises solid phase extraction.

13. The method of claim 10, wherein the separation step further comprises ion mobility spectrometry.

14. The method of claim 10, wherein the sample is a biological sample.

15. The method of claim 10, wherein deuterated 25OHD2 is added to the sample as an internal standard.

16. The method of claim 10, wherein the liquid chromatographic mobile phases comprise water and methanol.

17. The method of claim 10, wherein the stationary phase is a cyano stationary phase.

18. The method of claim 10, wherein the liquid chromatographic separation employs a solvent gradient curve.

19. The method of claim 18, wherein the liquid chromatographic separation employs a convex solvent gradient curve.

* * * * *